United States Patent
Tan et al.

(10) Patent No.: US 6,867,304 B1
(45) Date of Patent: Mar. 15, 2005

(54) PHOTOINITIATORS FOR TWO-PHOTON INDUCED FREE-RADICAL POLYMERIZATION

(75) Inventors: Loon-Seng Tan, Centerville, OH (US); Ramamurthi Kannan, Cincinnati, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 10/784,312

(22) Filed: Feb. 23, 2004

Related U.S. Application Data

(60) Provisional application No. 60/484,732, filed on Jul. 3, 2003.

(51) Int. Cl.[7] .............................................. C07D 277/66
(52) U.S. Cl. ...................................... 548/156; 548/160
(58) Field of Search ................................. 548/156, 160

(56) References Cited

U.S. PATENT DOCUMENTS

| 6,100,405 A | 8/2000 | Reinhardt |
| 6,300,502 B1 | 10/2001 | Kannan |

*Primary Examiner*—Kamal Saeed
(74) *Attorney, Agent, or Firm*—Charles E. Bricker; Fredric L. Sinder

(57) ABSTRACT

Provided are new TPA chromophores of the formula:

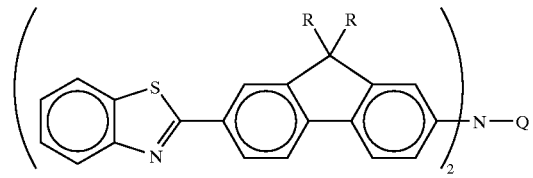

wherein R is an alkyl group having 1 to 20 carbon atoms and Q is —$C_6H_{13}$, —$CH_2$—$C_6H_5$, or —$C_6H_{11}$.

4 Claims, No Drawings

PHOTOINITIATORS FOR TWO-PHOTON INDUCED FREE-RADICAL POLYMERIZATION

CROSS REFERENCE TO RELATED APPLICATION

This application claims priority of the filing date of Provisional Application Ser. No. 60/484,732, filed Jul. 3, 2003.

RIGHTS OF THE GOVERNMENT

The invention described herein may be manufactured and used by or for the Government of the United States for all governmental purposes without the payment of any royalty.

BACKGROUND OF THE INVENTION

The present invention relates to chromophores with very large two-photon absorption cross-sections.

Two-photon or multiphoton absorption occurs through the simultaneous absorption of two or more photons via virtual states in an absorbing medium, with the former being more common. For a given chromophore, these absorption processes take place at wavelengths much longer than the cut-off wavelength of its linear (single-photon) absorption. In the case of two-photon absorption (TPA), two quanta of photons may be absorbed from a single light source (degenerate TPA) or two sources of different wavelengths (non-degenerate TPA). Although multiphoton absorption processes have been known since 1931, this field remained dormant largely due to the lack of TPA-active materials with sufficiently large cross-sections. In the mid-1990s, several new classes of chromophores exhibiting very large effective TPA cross-section ($\sigma_2'$) values were reported. In conjunction with the increased availability of ultrafast high-intensity lasers, the renewed interest has not only sparked a flurry of activities in the preparation of novel dye molecules with enhanced $\sigma_2'$ values, but also many previously conceived applications based on TPA process in photonics and biophotonics are now enabled by these new chromophores. It is important to recognize the following features of two-photon materials technology: (a) upconverted emission, whereby an incident light at lower frequency (energy) can be converted to an output light at higher frequency, for instance, IR to UV-Vis upconversion; (b) deeper penetration of incident light; (c) highly localized excitation allowing precision control of in-situ photochemical events in the absorbing medium, thereby minimizing undesirable activities such as photodegradation or photobleaching; (d) fluorescence when properly manipulated allows information feedback. It is anticipated that further ingenious utilization of these basic characteristics will lead to practical applications other than those already emerged in such diverse areas as fluorescence imaging, data storage, eye and sensor protection, microfabrication of microelectromechanical systems (MEMS), photodynamic therapy, etc.

Accordingly, it is an object of the present invention to provide new TPA chromophores.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided new TPA chromophores of the formula:

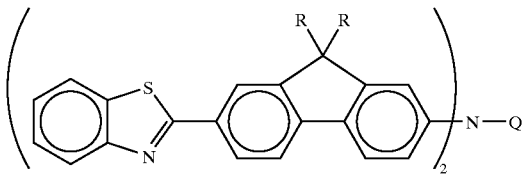

wherein R is an alkyl group having 1 to 20 carbon atoms and Q is —$C_6H_{13}$, —$CH_2$—$C_6H_5$, or —$C_6H_{11}$.

The chromophores of this invention can be synthesized following the procedures given in the following Examples which illustrate the invention:

EXAMPLE 1

2,7-Dibromofluorene

To a mechanically stirred mixture of fluorene (113.76 g., 0.68 mol.), iodine (1.96 g., 0.0077 mol.), and methylene chloride (750 ml), bromine (74 ml, 1.44 mol.) diluted with methylene chloride (100 ml) was added dropwise at room temperature over a period of 1.5 hours. After 5 minutes, a solution of sodium bisulfite (15.0 g.) in water (100 ml) was added and the mixture was stirred for 30 minutes, when the mixture became colorless. Water (750 ml) was then added, and methylene chloride was distilled off. The product slurry was filtered and the product was air-dried, 220.5 g., m.p. 156–160° C. This material was used in the next step without further purification.

EXAMPLE 2

9,9-Diethyl-2,7-dibromofluorene

To a mechanically stirred mixture of 2,7-dibromofluorene (66.5 g., 0.205 mol.), powdered potassium hydroxide (56.0 g., 1.0 mol.), potassium iodide (3.4 g.) and DMSO (150 ml), cooled to 10° C., ethyl bromide (40 ml, 58.4 g. 0.536 mol.) was added dropwise over 45 minutes. The mixture turned from red to light purple. After allowing the temperature to warm to 20° C., the mixture was left overnight to stir and poured into water, 77.0 g. (98.7% yield), m.p. 144–153° C. The product was then recrystallized from hexane (550 ml) with charcoal treatment, and collected in two crops, m.p. 154–157° C. and 153–154° C., totaling 60.36 g. (77.4% yield).

EXAMPLE 3

9,9-Diethyl-7-bromo-fluorene-2-carboxaldehyde

To a mechanically stirred solution of 9,9-diethyl-2,7-dibromofluorene.(59.38 g., 0.1563 mol.), in THF (325 ml), cooled in dry ice-ethanol bath, n-butyl lithium (104 ml of 1.6M solution in hexanes, 0.1664 mol, 1.06 eq.) was added dropwise over 25 minutes. After 20 minutes, DMF (17 ml, 0.22 mol.) in THF (30 ml) was added, and the mixture was stirred in the cooling bath for 1.5 hours, and outside the bath for 1 hour. The reaction was then cooled to 5° C., and treated with hydrochloric acid (12.5 of concentrated hydrochloric acid diluted with 50 ml water). The mixture was diluted with 200 ml of toluene, and the aqueous phase was separated and extracted with 200 ml of toluene. The combined organic phase was washed with dilute sodium bicarbonate solution, dried over magnesium sulfate and concentrated. The residual solids were recrystallized from heptane-ethyl acetate (9:1), to get colorless solids, 40.29 g. (78.4% yield)

m.p. 126–128° C. The mother liquor after chromatography over 150 g. silica gel, elution with 1:1 heptane-toluene, and trituration of residual solids in hexanes gave additional product, 6.56 g. (12.8% yield, total 91% yield), m.p. 126–128° C. Mass Spectrum (m/z): 328, 330, (M$^+$). A sample for analysis was prepared by recrystallization from hexanes, m.p. 127–129° C. Anal. Calcd. for $C_{18}H_{17}BrO$, C, 65.55, H, 5.20, and Br 24.27%. Found, C, 65.60, H, 5.51, and Br, 24.71%.

EXAMPLE 4

2-(7-Bromo-9,9-diethylfluoren-2-yl)benzothiazole

A mixture of 9,9-diethyl-7-bromo-fluorene-2-carboxaldehyde (49.35 g., 0.15 mol.), 2-aminothiophenol (20 ml. 0.187 mol., 1,25 eq.), and DMSO (110 ml) was heated in an oil bath to a bath temperature of 195° C., held there for 45 minutes, and then poured into water. The separated solids were collected, reslurried in 1:4 acetic acid-water (1000 ml.) filtered, and washed with water and dilute sodium bicarbonate solution. These solids, 80.05 g., were then reslurried in hot ethanol, (600 ml), cooled and filtered to get the product benzothiazole, 45.69 g., m.p. 133.6–135° C. An additional 6.6 g., m.p. 134.6–135.5° C., was obtained by chromatography of the ethanol filtrate. Total recovery was 52.29 g. (80.3% yield). Mass Spec: m/z 433, 435, (M$^+$). Anal. Calculated for $C_{24}H_{20}BrNS$: C, 66.37; H, 4.64; Br, 18.40; N, 3.23; S, 7.37%. Found: C, 66.46; H, 4.52; Br, 18.54; N, 3.14; S, 7.19%.

EXAMPLE 5

Bis-(7-benzothiazol-2-yl-9,9-diethylfluoren-2-yl) hexylamine

A mixture of 2-(7-bromo-9,9-diethylfluoren-2-yl) benzothiazole (example 4; 8.68 g, 20 mmol.), 1-hexylamine (1.32 ml, 10 mmol.), and toluene (200 ml) was heated to reflux under nitrogen, and toluene (10 ml) was distilled off. The mixture was cooled to 75° C., and sodium t-butoxide (5.57 g, 58 mmol.), 1.1'-bis(diphenylphosphino)ferrocene (0.4 g, 0.8 mmol.), and bis(dibenzylideneacetone)palladium (0) (0.46 g, 0.8 mmol.) were then added. The reaction mixture was then heated to 100° C., and held at this temperature for 24 hours. After cooling, the reaction mixture was diluted with 600 ml toluene, and the toluene solution was washed with water (2×300 ml). After drying over magnesium sulfate, the solution was filtered and concentrated. The residue (10.51 g), was chromatographed over alumina. Elution with toluene-heptane (1:1), gave the product, which was recrystallized from hexanes; 5.29 g (66% yield), m.p. 107.5–109° C. Mass spectrum (m/z): 807 (M$^+$). $^1$H NMR (CDCl$_3$; δ in ppm): 0.21–0.66 (t, 12H), 0.71–1.04 (t, 3H), 1.08–1.57 (m, 8H), 1.61–2.30 (m, 8H), 3.63–4.02 (t, 2H), 6.88–8.25 (m, 20 Ar—H). $^{13}$C NMR (CDCl$_3$; δ in ppm): 8.67, 14.02, 14.14, 22.58, 22.63, 26.81, 27.47, 31.56, 31.62, 32.80, 52.73, 56.33 (sp$^3$ C), 115.74, 119.11, 119.54, 121.24, 121.35, 121.47, 122.88, 124.86, 126.22, 127.34, 131.20, 133.99, 134.89, 144.73, 148.39, 150.32, 152.05, 154.27, 168.87 (sp$^2$ C). Anal. Calcd. for $C_{54}H_{53}N_3S_2$: C, 80.25%; H, 6.61%; N, 5.19%; S, 7.93%. Found: C, 80.22%, H, 6.82%, N, 5.03%, S, 7.87%.

EXAMPLE 6

Bis(7-benzothiazol-2-yl-9,9-diethylfluoren-2-yl) cyclohexylamine

A mixture of 2-(7-bromo-9,9-diethylfluoren-2-yl) benzothiazole (example 4; 8.54 g, 219.7 mmol.), cyclohexylamine (0.85 ml, 7.4 mmol.), and toluene (150 ml) was dried under nitrogen, by heating to reflux and distilling off toluene until the distillate was clear, and then cooled to 75° C. Bis(dibenzylideneacetone)palladium (0) (0.45 g, 0.8 m.mole), 1,1'-bis(diphenylphosphino)ferrocene (0.44 g, 0.8 mmol.), and sodium t-butoxide (5.49 g, 57 mmol.) were then added and the mixture was heated to 90° C. After 23 hours at this temperature, the mixture was allowed to cool to room temperature, and the separated solids (6.14 g) were filtered. The filtrate was washed with water, dried and concentrated. The residue was mixed with the above solids, and the mixture was chromatographed over silica gel. Ethyl acetate (1%)-toluene eluted the desired product which was recrystallized from a mixture of toluene and isopropanol yielding bright yellow solids, 4.21 g, (71% yield), m.p. 262.4–263.8° C. Mass spectrum (m/z): 805 (M$^+$). $^1$H NMR (CDCl$_3$; δ in ppm): 0.19–0.61 (t, 12H), 0.89–2.29 (m, 18H), 3.81–4.13 (m, 1H), 6.67–8.24 9 m, 20 Ar—H). $^{13}$C NMR (CDCl$_3$; δ in ppm): 8.61, 8.78, 25.89, 26.21, 31.97, 32.80, 56.30, 57.25 (sp$^3$ C), 117.52, 119.22, 120.95, 121.44, 121.50, 122.82, 124.89, 126.25, 127.28, 131.23, 134.43, 134.91, 144.79, 146.78, 150.49, 152.14, 154.27, 168.92 (sp$^2$ C). Anal. Calcd. for $C_{54}H_{51}N_3S_2$: C, 80.46%; H, 6.38%; N, 5.21%; S, 7.95%. Found: C, 80.47%; H, 6.64%; N, 5.10%; S, 7.92%.

EXAMPLE 7

Bis-(7-benzothiazol-2-yl-9,9-diethylfluoren-2-yl) benzylamine

A mixture of 2-(7-bromo-9,9-diethylfluoren-2-yl) benzothiazole (example 4; 7.01 g, 16 mmol.), benzylamine (0.81 ml, 7.4 mmol.), and toluene (150 ml) was heated to reflux under nitrogen into a dean-stark trap until the mixture was dry, and then cooled to 75° C. Bis (dibenzylideneacetone)palladium (0) (0.34 g, 0.6 mmol.), 1.1'-bis(diphenylphosphino)ferrocene (0.33 g, 0.6 mmol.) and sodium t-butoxide (4.09 g, 43 mmol.) were then added and the mixture was heated to 90° C. After 18 hours at this temperature, the mixture was allowed to cool to room temperature, and the separated solids were collected. The filtrate was diluted with toluene, and the toluene solution was washed with water, dried and concentrated. The residue was mixed with the solids above, and the mixture was chromatographed over silica gel. Elution of the column with 2%-ethyl acetate-toluene gave the product, which was then recrystallized from a mixture of toluene and isopropanol to afford a bright yellow solid; 2.28 g, (37% yield), m.p. 174.5–176.3° C. Mass spectrum (m/z): 813 (M$^+$). $^1$H NMR (CDCl$_3$; δ in ppm): 0.16–0.51 (t, 12H), 1.75–2.21 (m, 8H), 5.16 (s, 2H), 7.00–8.21 (m, 25 Ar—H). $^{13}$C NMR (CDCl$_3$; δ in ppm): 8.61, 32.8, 56.4 (sp $^3$C), 115.74, 119.19, 119.57, 121.24, 121.38, 121.52, 122.88, 124.92, 126.25, 126.82, 126.97, 127.31, 128.21, 128.58, 129.01, 131.26, 134.28, 134.89, 137.85, 138.74, 144.65, 148.28, 150.38, 152.02, 154.24, 168.90 (sp$^2$C). Anal. Cald. for $C_{55}H_{47}N_3S_2$: C, 81.14%; H, 5.82%; N, 5.16%; S, 7.87%. Found: C, 81.11%; H, 6.45%, N, 4.54%, S, 7.22%.

The TPA values of the chromophores are shown in the following table. The TPA and linear optical properties of the chromophores AF-240, AF-350 and AF-380 are include for comparison:

| Chromophore from Example | $\lambda_{max}$ (nm) Linear Abs. (Upconv. Emission.) | $\beta$ cm/GW at 0.2 mol/L | $\sigma_2'$ ($\times 10^{-48}$ $\frac{cm^4 \cdot sec}{ph \cdot molecule}$) | $\sigma_2'/MW$ ($\times 10^{-50}$ $\frac{cm^4 \cdot sec \cdot mole}{ph \cdot molecule \cdot g}$) |
|---|---|---|---|---|
| (AF-240)* | 395 (479) | 4.7 | 97.5 | 19 |
| (AF-380)** | 428 (513) | 11.1 | 228.6 | 21.2 |
| (AF-350)*** | 392 (490) | 13.5 | 238.1 | 18.3 |
| 5 | 392 (496) | 5.3 | 108.1 | 13.4 |
| 6 | 400 (484) | 8.2 | 169 | 21.0 |
| 7 | 412 (476) | 5.7 | 117 | 14.4 |

*(7-benzothiazol-2-yl-9,9-diethylfluoren-2-yl)diphenylamine
**Tris-7-(2-benzothiazolyl)-9,9-diethyl-2-fluorenylamine
***(N,N,N-tris[4-(7-benzothiazol-2-yl-9,9-diethylfluoren-2-yl)phenyl]amine

Having thus described exemplary embodiments of the present invention, it should be noted by those skilled in the art that the disclosures herein are exemplary only and that alternatives, adaptations and modifications may be made within the scope of the present invention.

We claim:

1. A chromophore of the formula:

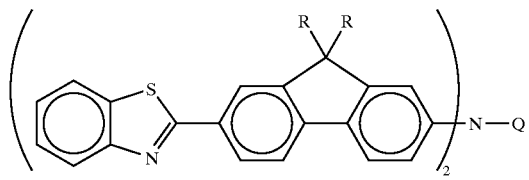

wherein R is an alkyl group having 1 to 20 carbon atoms and Q is —$C_6H_{13}$, —$CH_2$—$C_6H_5$, or —$C_6H_{11}$.

2. The chromophore of claim 1 wherein each R is ethyl and Q is —$C_6H_{13}$.

3. The chromophore of claim 1 wherein each R is ethyl and Q is —$CH_2$—$C_6H_5$.

4. The chromophore of claim 1 wherein each R is ethyl and Q is —$C_6H_{11}$.

* * * * *